United States Patent [19]
Stiller et al.

[11] 3,986,392
[45] Oct. 19, 1976

[54] APPARATUS FOR TESTING DYNAMIC IMPACT RESISTANCE OF A TIRE

[75] Inventors: Harald L. Stiller, Grosse Pointe Park; Serhij Lazurenko, Grosse Pointe Woods; Haig D. Tarpinian, Grosse Pointe Park, all of Mich.

[73] Assignee: Uniroyal Inc., New York, N.Y.

[22] Filed: June 11, 1975

[21] Appl. No.: 585,970

[52] U.S. Cl. .................................................. 73/146
[51] Int. Cl.² ........................................ G01M 17/02
[58] Field of Search .................... 73/146, 91, 81, 82

[56] References Cited
UNITED STATES PATENTS

| | | | |
|---|---|---|---|
| 3,095,733 | 7/1963 | Sjostrom | 73/91 |
| 3,599,486 | 8/1971 | Pernau | 73/146 |

OTHER PUBLICATIONS

O'Neil et al., "Dynamic Plunger Testing", MATERIAL RESEARCH & STANDARDS, vol. 10, No. 6 (June 1970), pp. 30–32, 73–146.

Draves, Jr., et al., "B. F. Goodrich Dynamic Bruise Tester", MATERIALS RESEARCH & STANDARDS, vol. 10, No. 6 (June 1970), pp. 26–29.

*Primary Examiner*—Charles A. Ruehl
*Attorney, Agent, or Firm*—Philip Rodman

[57] ABSTRACT

The dynamic impact resistance of an inflated tire is tested by freely supporting the tire for rotation on a fixed frame and penetrating the tire with an impact plunger protractible through an opening in the periphery of a power driven test wheel as the wheel periphery rotates against the tire tread. The plunger can be entirely retracted in the peripheral opening of the test wheel to a non-impinging position following one impact with the tire, or the plunger can be set to remain in a protracted position to impact the tire tread a designated number of times before being retracted. A plug can be substituted for the plunger to seal the peripheral opening in the test wheel.

23 Claims, 8 Drawing Figures

APPARATUS FOR TESTING DYNAMIC IMPACT RESISTANCE OF A TIRE

This invention is directed to new and useful improvements in apparatus for evaluating the performance of pneumatic tires and more particularly to an apparatus for impacting a rotating tire to test the dynamic impact resistance of the tire.

Pneumatic tires and especially automobile tires under normal usage experience continuous wear, continuously varying stresses, and continuously varying temperature changes. The average automobile tire despite its subjection to these conditions of adversity is expected to have a consistently high level of performance over a predetermined number of miles traveled.

Technological innovations in the tire industry have led to a diversity of ever changing materials and methods used in the construction and manufacture of tires. Systematic evaluation of these materials and methods is usually an ongoing collateral procedure in the tire industry.

Numerous approaches exist for evaluating tire performance such as road testing a tire over a given terrain. The data obtained from a road test is often directed to the durability, strength and life expectancy, etc. of the tire. Valuable insight into the potential performance of a tire can also be obtained by testing the tire in a laboratory, where test conditions can normally be accurately controlled and easily repeated or varied for substantiation or comparison.

One known method of testing the impact resistance of a tire in a laboratory is to mount the tire in an inflated condition on a stand in static position and subject the tire to an impact, usually delivered by a cylindrical steel plunger ram-driven into the tire tread until either the carcass ruptures or the tread bottoms against the wheel well. The National Highway Traffic Safety Administration (NHTSA) under Standard 109 has specified acceptable breaking energy values for tire tread under static conditions. Passenger tires of recent construction, especially those having belts under the tread, have been found to exceed by 200 to 300% the strength requirements established by NHTSA Standard 109. Consequently the static rupture test along with NHTSA Standard 109 have been criticized as lacking sufficient correlation with the forces that are present when a tire dynamically strikes an object under actual road conditions.

A known alternative to such static testing is a dynamic rupture test that is performed on the road. The tire being tested is mounted on an automobile for movement along a special courseway containing a dynamic rupture machine. The rupture machine is embedded in the ground but includes an upwardly projecting impact pin having a hemispherical head free of cutting edges or points. The dynamic rupture test is designed to produce concentrated strains and deformation of a tire than can cause breakage, splitting or other types of impact-rupture damage to a tire ply or tire fabric.

Before a tire is subject to impact it has been found desirable to provide a preliminary warm-up run at a suitable speed such as 90 miles per hour. After warm-up the tire is driven over the impact pin of the rupture machine at another suitable speed such as 60 miles per hour. Generally the dynamic rupture machine is used for impacting only one tire of the automobile, preferably a front tire. Therefore immediately after impact the front test tire moves over a pin retraction lever that pivots the impact pin into a ground level recess of the rupture machine before the rear tires pass over the machine.

Dynamic impact tests of this nature are quite costly requiring highly qualified test drivers and a special courseway. Such tests are time consuming in terms of man hours expended and are also uncertain since they do not always yield an accurate impact between the pin and the tire tread.

It is therefore desirable to provide an apparatus for delivering a dynamic impact to a tire which does not require actual road testing, special courseways, skilled drivers and the expenditure of many man hours yet yields an accurate impact to a rotating tire at less overall cost than was previously obtainable. It is also desirable that such an apparatus be functionally operable in a laboratory.

Among the several objects of the present invention may be noted the provision of a novel apparatus for delivering a dynamic impact to a tire; a novel test apparatus for dynamically impacting a tire in a laboratory; a novel dynamic impact apparatus which can warm up a tire, impact the tire a predetermined number of times and continue to rotate the tire without further impact; a novel dynamic impact test apparatus for a laboratory which can provide selected depths of penetration of the tire at impact; a novel dynamic impact apparatus which can be controlled to accurately impact a tire at its tread center or any other point on the tread; a novel dynamic impact apparatus for a tire that simulates actual driving conditions; and a novel method for testing the dynamic impact resistance of a tire.

Other objects and features will be in part apparent and in part pointed out hereinafter.

The present invention relates to a novel laboratory test apparatus for delivering one or more dynamic impacts to a tire to evaluate the impact resistance of the tire tread and carcass. The apparatus, in a preferred embodiment, includes a motor driven test wheel that has a generally circular peripheral surface arranged to engage the tread of an axially mounted tire freely rotatable on a fixed stand to frictionally rotate the tire. Since a given number of revolutions of the test wheel correspond to a mile of tire travel, any suitable known counting devices associated with the test wheel can be used to record tire mileage and speed during the test. The test wheel includes a recessed impact plunger that is protractible through an opening in the wheel periphery for impact with the tread of the frictionally rotating tire. The impact plunger, which is also retractible in the wheel opening to a non-impinging position after tire impact, is mounted between the wheel periphery and a hub of the test wheel. Movement of the plunger is affected by a cam that is actuatable by a double acting pneumatic cylinder also mounted on the test wheel. Activation of the pneumatic cylinder during rotation of the test wheel causes the cam to rotate and shift the impact plunger into either its protracted or retracted position.

In carrying out an impact test a tire is inflated to a predetermined pressure and allowed to sit or condition for a fixed time at a preselected temperature. The test wheel imposes a desired load on the tire in a known manner and a warm-up run is taken at a predetermined speed for a predetermined amount of tire travel. The pneumatic cylinder is activated to protract the plunger to impact the tire at a zone of contact between the tire tread and the test wheel. After one or more impacts the pneumatic cylinder is activated to retract the plunger to its non-impinging position where it remains if no further impacts are required. An indicating substance may be provided on the plunger to facilitate location on the tire tread of the point or points of impact.

The invention accordingly comprises the constructions hereinafter described, the scope of the invention being indicated in the following claims.

In the accompanying drawings in which one of various possible embodiments of the invention is illustrated.

FIG. 3 is a sectional view taken along the line 3—3 of FIG. 2;

Corresponding reference characters indicate corresponding parts throughout the several views of the drawings.

Figure 1:
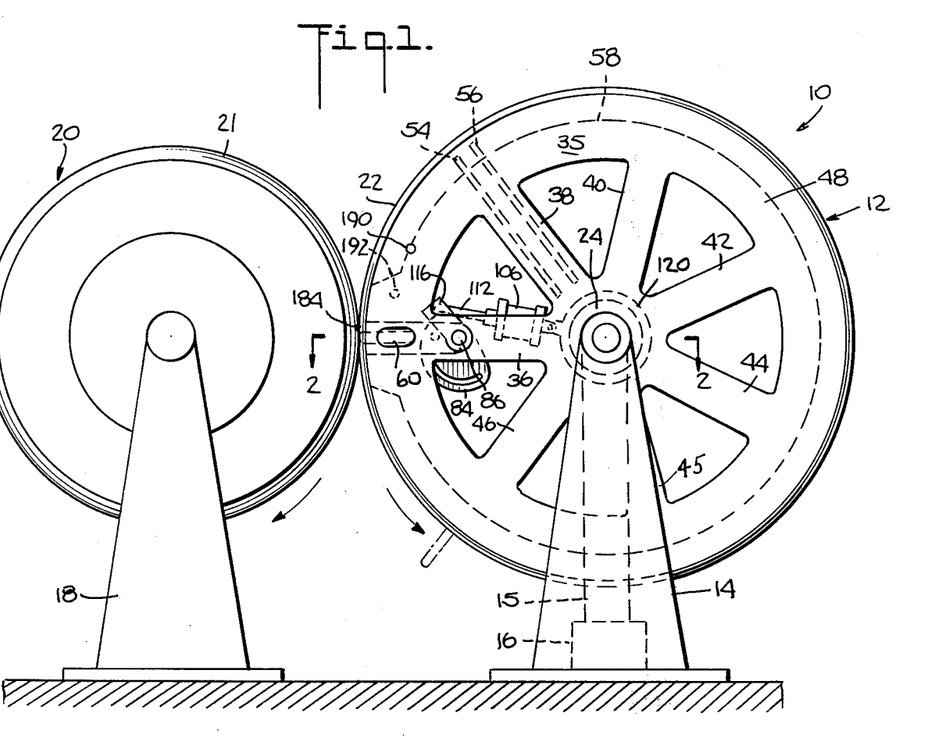
FIG. 1 is a front elevational view of a dynamic impact apparatus incorporating one embodiment of the present invention.

Referring to the drawings for a detailed description of the present invention an apparatus for testing the dynamic impact resistance of a tire which incorporates one embodiment of the present invention is generally indicated by the reference number 10 in FIG. 1. The apparatus 10 comprises a test wheel 12 that is generally similar to a class of wheels commonly known as road wheels. The test wheel 12 is supported on a frame 14 for rotation by any suitable known variable speed drive means such as a motor 16. A driving connection 15 between the motor 16 and the test wheel 12 is conventional and for purposes of clarity is shown dotted in FIG. 1. The apparatus 10 further includes a frame 18 rotatably supporting a tire 20 with a tread portion 21 in frictional engagement with a peripheral portion 22 of the test wheel 12.

The test wheel 12, which is made of steel or any other suitable material, comprises a hub portion 24 conventionally keyed to a shaft 26. Opposite journal end portions 28 and 30 (FIGS. 2 and 5) of the shaft 26 engage bearings 32 and 34, such as SKF Number 1318K, housed in the frame 14 in any suitable known manner.

Figure 2:
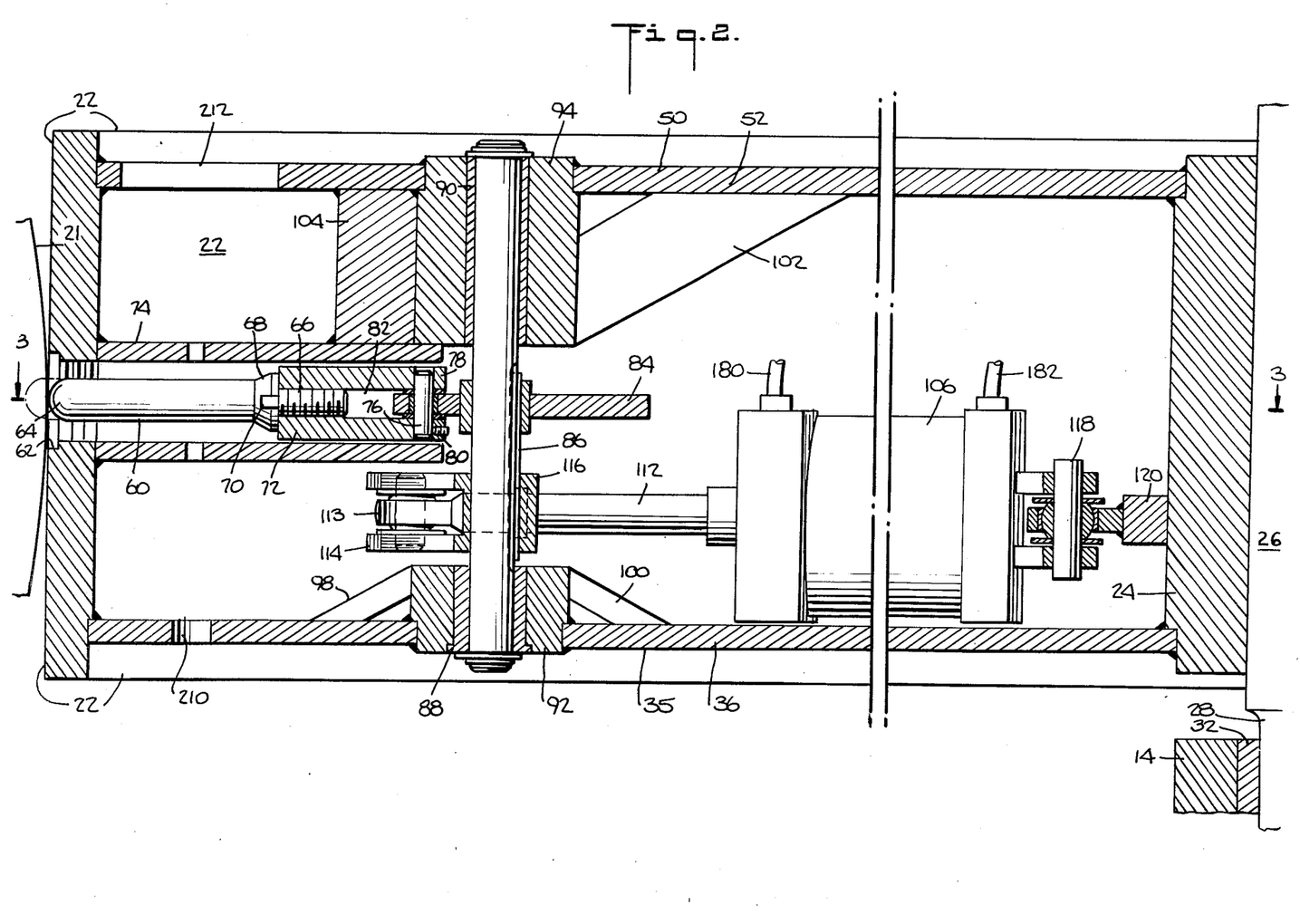
FIG. 2 is a sectional view taken along the line 2—2 of FIG. 1.
Figure 5:
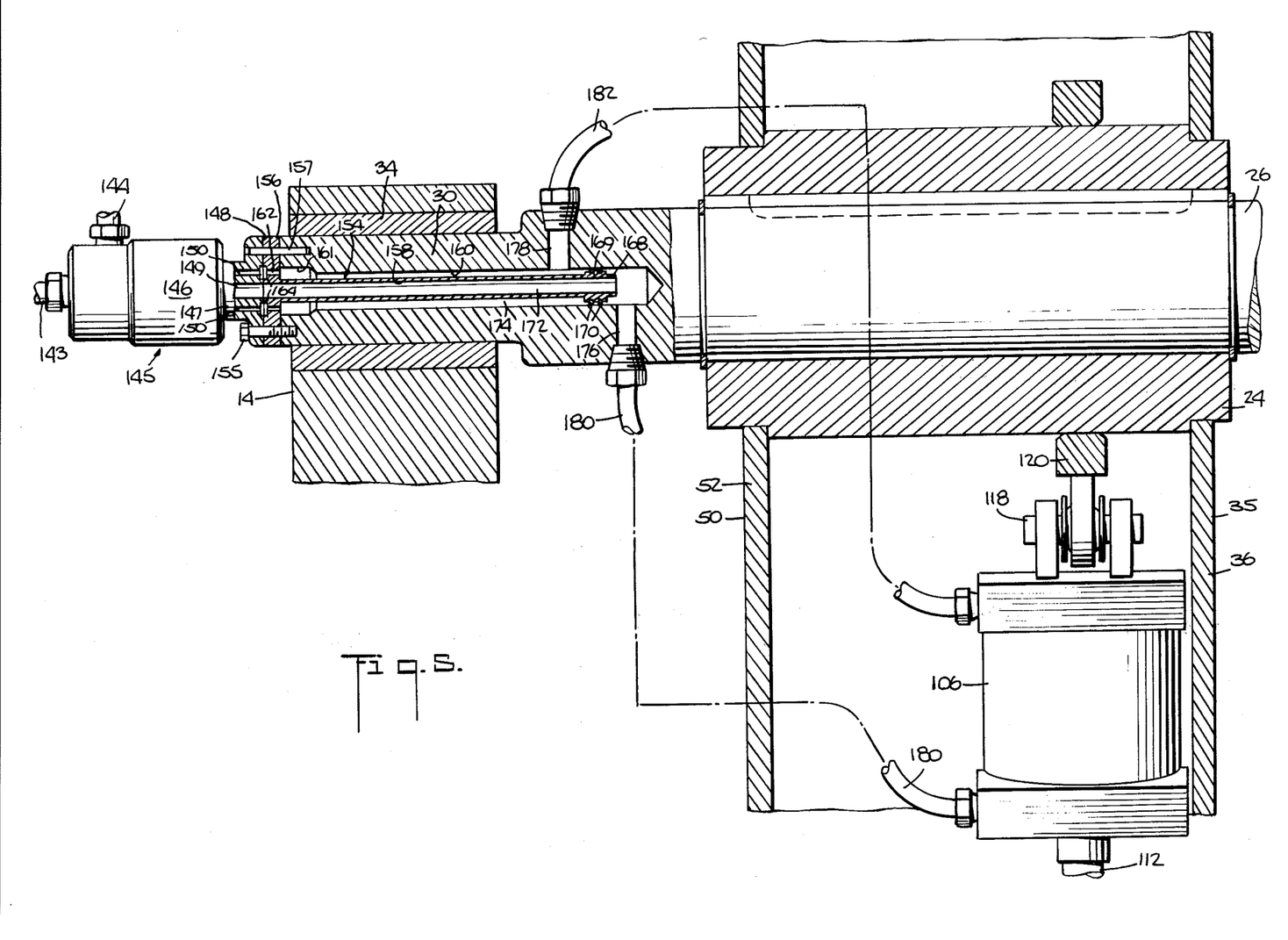
FIG. 5 is an enlarged fragmentary sectional view of the dynamic impact apparatus showing a portion of the pneumatic system between the rotating union and the pneumatic cylinder.

The test wheel 12 further includes a side plate 35 having a plurality of spoke portions such as 36, 38, 40, 42, 44, 45 and 46 extending radially from the hub 24 to an annular region 48. An opposite side plate 50, shown fragmentarily in FIGS. 2 and 5, is spaced from and substantially similar to the side plate 35. For example the side plate 50 has a spoke portion 52 opposite the spoke portion 36 of the side plate 35 (FIGS. 2 and 5). The side plate 50 also contains opposite spoke portions (not shown) corresponding to the spoke portions 38, 40, 42, 44, 45 and 46. A pair of spaced reinforcing webs 54 and 56 (FIG. 1) span the side plates 35 and 50 at the spoke portion 38. Similar reinforcing webs (not shown) span the side plates 35 and 50 at the spoke portions 40, 42, 44, 45 and 46. The peripheral portion 22 of the test wheel 12 also spans the side plates 35 and 50 as shown in FIG. 2. A substantially annular rib 58 (FIG. 1) depends from the inner perpherial portion 22 midway between the side plates 35 and 50 for connection, as by welding, to the radial extremity portions of the reinforcing webs such as 54 and 56.

The test wheel 12 also includes means for impacting a tire comprising an impact member or plunger 60 disposed between the spoke portions 36 and 52 in alignment with an opening 62 in the wheel periphery 22. The plunger 60 comprises a smooth hemispherical free end portion 64, an opposite threaded portion 66 and an intermediate skirt portion 68. The skirt portion 68 includes a pair of oppositely formed radial slots 70, 70 for receiving any known suitable spanner wrench (not shown) having teeth that fit into the slots 70, 70. The threaded portion 66 of the plunger 60 engages a generally cylindrical displacement member 72 slidably disposed in an elongated annular collar 74 welded to the wheel periphery 22 at the opening 62 such that the plunger 60 is aligned with the opening 62.

A cam follower rod 76 is supported in oppositely spaced side portions 78, 80 of the displacement member 72. The space between the side portions 78 and 80 defines a clearance slot 82. A cam member 84 is keyed to a shaft 86 rotatably supported by a pair of end bearings 88 and 90 respectively housed in the spoke portions 36 and 50 at the support pieces 92 and 94 (FIG. 2). The shape of the cam 84 is described as a uniformly accelerated motion cam in Machinery Handbook, 19th edition, 1971, page 714 published by Industrial Press. The cam member 84 comprises an arcuate cam slot 96 having end portions 95 and 97 the slot 96 being engageable with the follower rod 76 carried by the displacement member 72. It should be noted that the longitudinal axis of the plunger 60, the central axis of the follower rod 76 and the central axis of the shaft 86 are coplanar as best seen in FIG. 3 which shows the edge view of a plane P passing through the respective axes.

A pair of gussets 98 and 100 further reinforce the connection between the support piece 92 and the spoke portion 36 (FIG. 2). A gusset 102 and a brace member 104 reinforce the connection between the support piece 94 and the spoke portion 52. The support piece 94 and the brace member 104 also brace the annular collar 74. A pair of gussets 105 and 107 (FIG. 3) further brace the annular collar 74 against the wheel periphery 22.

A pneumatic double acting cylinder 106 such as manufactured by Miller, Model No. A84-B includes a piston 110 (FIG. 7) having a piston rod 112 projecting from one end of the cylinder. A remote end 113 of the piston rod 112 is pivoted to a U-shaped end 114 of a clevis member 116 that is keyed to the shaft 86. The cylinder 106 is pivotally connected at 118 to a yoke member 120 that is affixed to the wheel hub 24 by welding and/or by fasteners such as 122.

Figures 6, 7:
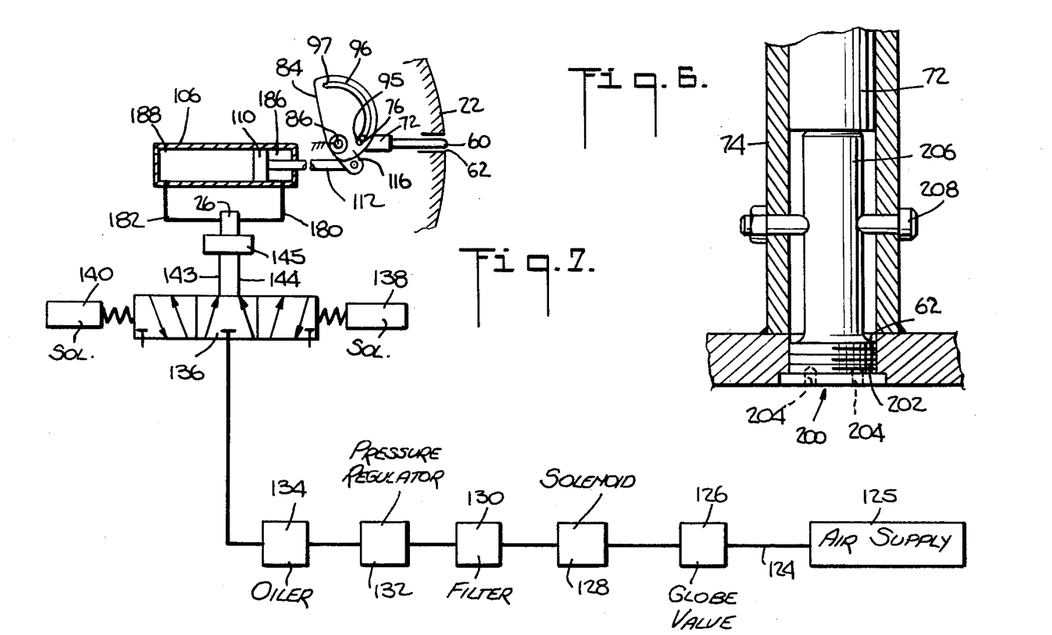
FIG. 6 is a fragmentary sectional view of a plug for the dynamic impact apparatus.
FIG. 7 is a simplified schematic diagram of the fluid circuit incorporated therein; and, FIG. 8 is a simplified schematic diagram of the electrical control circuit incorporated therein.

Referring to FIG. 7 the means for operating the pneumatic cylinder 106 comprise an air supply line 124 fed through an air supply source 125. The air supply line 124 includes a globe valve 126, a solenoid controlled valve 128 such as No. 581B-1-2 manufactured by M.A.C. Company, a filter 130, a pressure regulator 132, an oiler 134 and a valve 136 all of which are known components and therefore shown schematically. The valve 136 which is any suitable four-way valve such as No. 583B-1-2 manufactured by M.A.C. Company is actuatable through solenoids 138 and 140.

A pair of fixed air distribution lines 143 and 144 extend between the valve 136 and a rotating union 145 such as manufactured by Deublin Model No. 1550. As shown in FIG. 5 the rotating union 145 comprises a stationary barrel portion 146 and a neck portion 147 rotatably mounted within the barrel portion 146. The neck portion 147 has an end face 148 and comprises an elongated central opening 149 surrounded by a plurality of elongated satellite openings 150, the centers of which are concentric with the central opening 149.

An air tube member 154 (FIG. 5) comprises a flange portion 156 sandwiched between the neck portion 147 of the rotating union 145 and the journal end portion 30 of the shaft 26. A plurality of fasteners 155 and a pair of oppositely disposed locating pins 157 align and fasten the neck portion 147 and the flange portion 156 to the shaft 26. The air tube member 154 includes an elongated tube portion 158 that communicates with the central opening 149 in the neck portion 147 and extends from the flange portion 156 into an elongated axially bored hole 160 in the journal end portion 30 of the shaft 26. The bored hole 160 includes a counter bore portion 161. A plurality of satellite openings 162 in the flange 156 concentrically surround the elongated tube 158 for communication with the counter bore portion 161 on the shaft 26. The satellite openings 162 also communicate with the satellite openings 150 in the neck portion 147 through an annular channel 164 formed in the flange 156 and the end face 148 of the rotating union neck portion 147.

The elongated air tube 158 has a free end portion 168 containing a collar 169 formed or welded thereon to support any suitable gasketing such as O-rings 170 sealing against the wall portion of the bored hole 160. The air tube 158 thus positioned in the bored hole 160 defines an inner air chamber 172 and an annular outer chamber 174. The air chambers 172 and 174 respectively communicate with a pair of fluid ports 176 and 178 formed in the shaft 26 at the journal end portion 30. However, there is no intercommunication between the air chambers 172 and 174 due to the seal between the O-rings 170 and the bored hole 160. A pair of rotating fluid lines 180 and 182 connect the fluid ports 176 and 178 to the pneumatic cylinder 106.

In operating the apparatus 10 within a laboratory or other suitable test area it has been found desirable to maintain an ambient temperature of approximately 100°F. prior to running the wheel 12. The tire 20, which is inflated to a predetermined pressure, is allowed to become conditioned to the ambient temperature for a predetermined time period such as three hours. The tread portion 21 of the tire 20 and the wheel periphery 22 are brought into contact in a known manner to permit imposition of a predetermined load on the tire 20 by the test wheel 12. The motor 16 is activated to rotate the wheel 12 which simultaneously revolves the tire 20 due to frictional engagement between the wheel periphery 22 and the tire tread 21 at a contact area 184.

The test wheel 21 can be set to run at any suitable speed for any suitable length of time such as to provide a tire speed of 50 miles per hour for one-half hour.

During this initial running or warming up period the impact member 60 is in a retracted non-impinging position. The globe valve 126 is turned on and the valve 128 energized to permit air to flow through the air line 124 to the filter 130. The pressure regulator 132 controls the air pressure level through the oiler 134 to the valve 136. The speed of movement of the piston 110 in the air cylinder 106 is governed by the level of air pressure and we have found that an air pressure level of 90 psi is adequate when running the tire at 50 miles per hour.

When the solenoid 138 is energized the valve 136 permits air to flow through the fixed air distribution line 144 into the rotating union 145 through the central opening 149 to the inner air chamber 172 into the rotating fluid line 180 for delivery to one side 186 (FIG. 7) of the pneumatic cylinder 106. Air is simultaneously bled from another side 188 of the pneumatic cylinder 106 through the rotating fluid line 182 into the outer air chamber 174 through the satellite openings 162 into the annular channel 164 to the satellite openings 150 into the rotating union 145 to the fixed air distribution line 143 for exhaustion from the valve 136.

Figure 4:
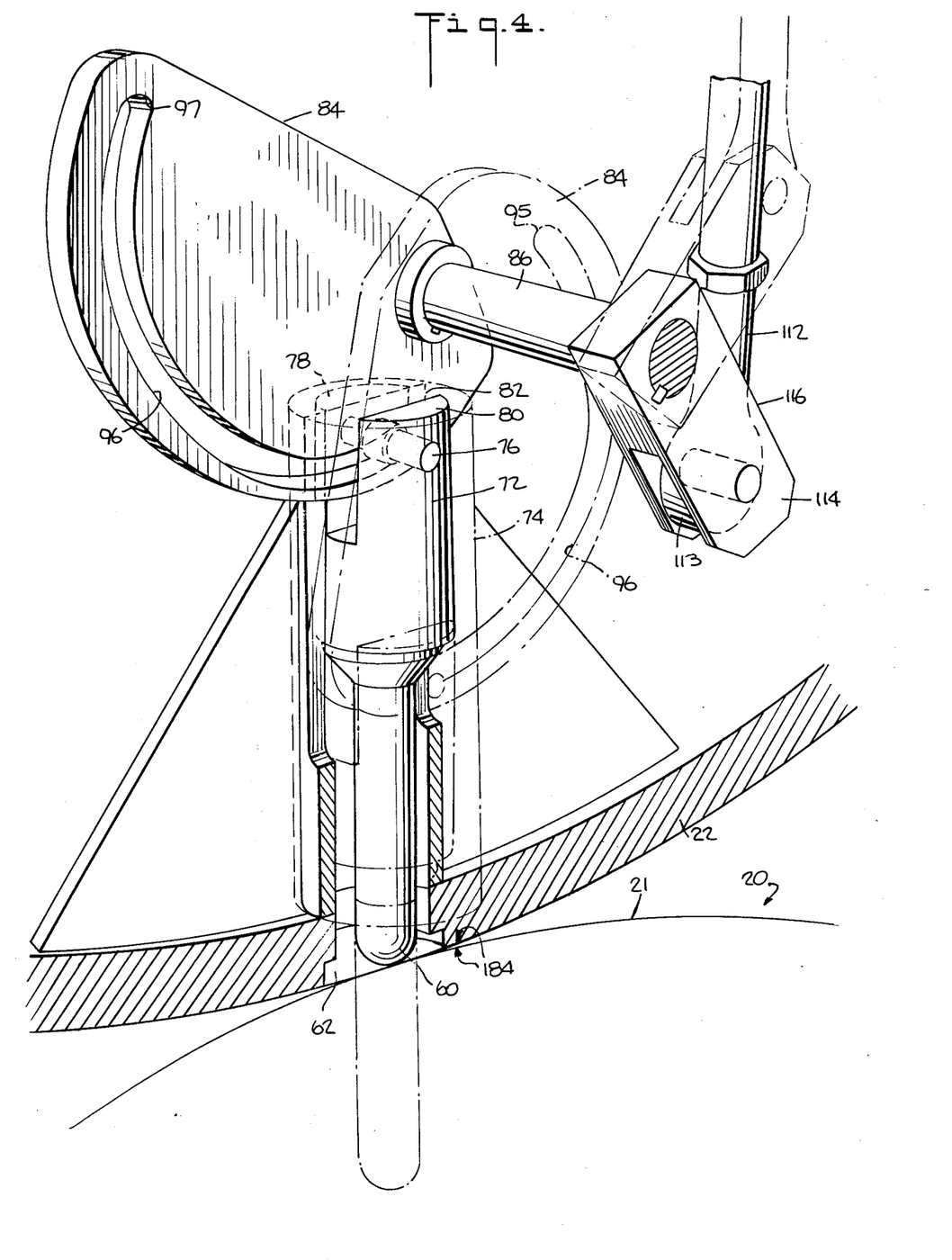
FIG. 4 is an enlarged fragmentary perspective view of an impact member included in the apparatus, and portions of a mechanism for protracting and retracting the impact member.

Referring to FIGS. 4 and 7, air entering the side 186 of the pneumatic cylinder 106 shifts the piston rod 112 to rotate the clevis 116 and the shaft 86 in a clockwise direction with respect to the axis of the shaft 86 and cause the cam member 84, which is keyed to the shaft 86, to likewise rotate in a clockwise direction. The cam slot 96 is thus moved relatively to the follower rod 76 until the cam slot end portion 97 is presented adjacent the follower rod 76, the cam member 84 moving into the clearance slot 82 of the annular collar 74. The cam member 84 thus causes the cam slot 96 to move the follower rod 76 and the displacement member 72 toward the wheel periphery 22 whereby the plunger 60 is protracted from the peripheral opening 62. Preferably the plunger 60 is fully protracted before it enters the frictional contact area 184 between the test wheel 12 and the tire 20. During impact the plunger 60 passes the contact area 184 to indent or penetrate the tread 21 and remains fully protracted throughout the impact.

If only one impact to the tire tread 21 is desired the plunger 60 is retracted to a non-impinging position before the next sequential pass through the contact area 184.

When the solenoid 140 is energized the valve 136 permits air to flow through the fixed air distribution line 143 through the rotating union 145 to the satellite openings 150, the annular chamber 164, and the satellite openings 162 into the outer air chamber 174 to the rotating fluid line 182 and into the side 188 of the pneumatic cylinder 106. Air is simultaneously bled from the side 186 of the cylinder 106 through the rotating fluid line 180 into the inner air chamber 172 through the central opening 149 into the rotating union 145 to the fixed air distribution line 144 for exhaustion from the valve 136.

Referring to FIGS. 5 and 7 the air entering the side 188 of the cylinder 106 causes the piston rod 112 to pivot the clevis 116 and the shaft 86 in a counterclockwise direction with respect to the axis of the shaft 86, enabling the cam member 84 to rotate on the shaft 86 in a counterclockwise direction. Counterclockwise movement of the cam member 84 causes the cam slot 96 to move relatively to the follower rod 76 such that the cam slot end portion 95 is presented adjacent the follower rod 76 whereas the cam slot end portion 97 is moved away from the follower rod 76. The cam member cam slot 96 thus moves the follower rod 76 and the displacement member 72 inwardly of the wheel periphery 22 to retract the plunger 60 within the peripheral opening 62 in a non-impinging position as shown in FIGS. 2, 3 and 4 before its next cyclic pass into the contact area 184.

Figure 8:
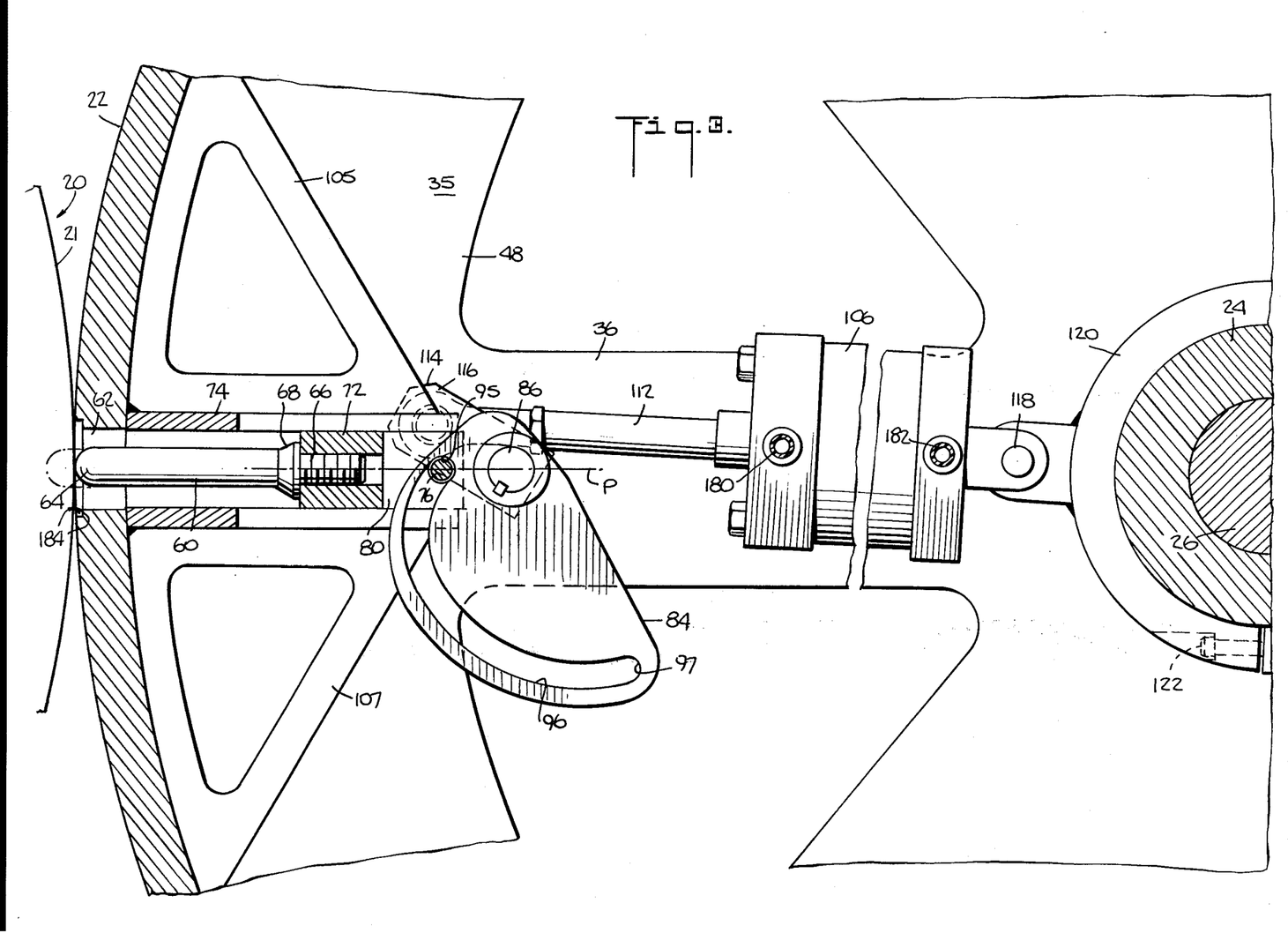

Delivery of one or more impacts by the plunger 60 to the tire tread 21 while the tire 20 is rotating is controlled by the circuit 300 shown in FIG. 8. The circuit 300 operates from a 120 volt, 60 cps power source 302 and includes an on-off selector switch 304, such as Cutler-Hammer 10250T3011-1-1 in series with the power source 302. The solenoid 128 of FIG. 7 is connected across the selector switch 304 and the power source 302. A normally open limit switch 306, such as Cutler-Hammer 10316H637, capable of being tripped in any suitable known manner by any suitable known triggering device 190 provided on the side plate 35 of the test wheel 12 (FIG. 1) interconnects with a selector switch 308 similar to the selector switch 304. The selector switch 308 is arranged to communicate with any suitable known counting device 310 having a count range up to 100 as the Cycl-Flex counter HZ170 manufactured by the Eagle Signal Company.

A normally closed electrical contact 312 and the solenoid 138 of FIG. 7 are connected across the selector switch 308 and the counter 310. A control relay 314 such as Cutler-Hammer D23MR22, and a normally open electrical contact 316 controlled by the relay 314 are connected across the limit switch 306, the contacts 312 and the solenoid 138. The limit switch 306 is also operable between the selector switch 304 and the control relay 314. A normally open electrical contact 317, also controlled by the relay 314, a limit switch 318 such as Cutler-Hammer 10316H187, a normally closed contact 320, controlled by the counter 310, a selector switch 322 similar to the selector switch 304, and the solenoid 140 of FIG. 7 are connected across the control relay 314 and the contacts 316. The limit switch 318 is capable of being tripped by a triggering device 192 (FIG. 1) similar to the triggering device 190, provided on the side plate 50 offset from the triggering device 190. The particular location of the triggering devices 190 and 192 on the side plates 35 and 50, or at any other suitable location, is a matter of choice. A normally open electrical contact 324 is connected across the limit switch 318 and the electrical contact 320. A control relay 326 similar to the control relay 314 is connected across the solenoid 140 and controls the electrical contacts 312 and 324.

When it is desired to impact the tire 20 one time only, the selector switches 304 and 322 are placed in closed positions and the selector switch 308 is left in an open position. Power from the source 302 is thus continuously transmitted to the solenoid 128 enabling air from the air supply 125 (FIG. 7) to flow through the line 124 to the valve 136.

As the test wheel 12 rotates, the triggering devices 190, 192 sequentially trip the respective limit switches 306 and 318. If the triggering device 192 should trip the limit switch 318 before the triggering device 190 trips the limit switch 306, current will not flow through the limit switch 318 because the contacts 317 are in their normally open position. When the limit switch 306 is closed by the triggering device 190 current flows through the upper branch of the switch 306 past the normally closed contacts 312 to the solenoid 138 which is energized to permit air to flow through the valve 136 to the side 186 (FIG. 7) of the cylinder 106 and protract the plunger 60 in a manner previously described. Once the solenoid 138 has been pulsed, the plunger 60 remains fully protracted until the solenoid 140 is energized. Current also flows through the lower branch of the limit switch 306 to the control relay 314 which causes the contacts 316 to close establishing a continuous flow of current through the contacts 316 and the control relay 314 even after the limit switch 306 assumes its normally open position. Continuous energization of the control relay 314 also causes the normally open contacts 317 to remain continuously closed. However the solenoid 140 is not energized due to the open circuit condition of the limit switch 318 and the normally open contacts 324.

When the limit switch 318 is sequentially closed by the triggering device 192 after the limit switch 306 has been closed by the triggering device 190, current flows through the contacts 317, past the limit switch 318, beyond the normally closed contacts 320 and the closed selector switch 322 to the solenoid 140 and the control relay 326. Energization of the solenoid 140 enables air to flow to the side 188 of the cylinder 106 through the valve 136 to retract the plunger 60 in a manner previously described. Energization of the control relay 326 causes the normally closed contacts 312 to open while causing the normally open contacts 324 to close. This establishes a continuous flow of current from the power source 302 to the solenoid 140 and the control relay 326 even after the limit switch 318 assumes its normally open position. Such continuous flow of current is via the contacts 317 and 324 which have been closed by energization of the respective relays 314 and 326, and the closed selector switch 322. With the solenoid 140 under continuous energization the plunger 60 is continuously held in a retracted position as previously described.

Any subsequent closing of the limit switch 306 by the triggering device 190 cannot provide energization of the solenoid 138 to cause protraction of the plunger 60 because the normally closed contacts 312 are maintained in an open condition by the control relay 326 which is being continuously energized as previously described.

To impact the tire 20 more than one time the selector switches 304, 308 and 322 are closed and the counter 310 is adjusted to establish the desired number of impacts, such as for example, ten impacts. Power from the source 302 is continuously transmitted to the solenoid 128 enabling air from the air supply 125 (FIG. 7) to flow through the line 124 to the valve 136. When the limit switch 306 is closed by the triggering device 190 (FIG. 1) a pulse of current flows through the upper branch of the limit switch 306 past the lower branch of the closed selector switch 308 to the counter 310 enabling it to record one count, and another pulse of current flows through the normally closed contacts 312 to the solenoid 138 to permit air to flow past the valve 136 (FIG. 7) to the cylinder 106 and protract the plunger 60 as previously described. The plunger 60 remains fully protracted until the solenoid 140 is energized. The counter 310 also receives a continuous flow of current through the upper branch of the closed selector switch 308 and causes the normally closed contacts 320 to remain continuously open. A pulse of current flowing through the lower closed branch of the limit switch 306 permits the relay 314 to be energized thereby setting up a closing of the normally open contacts 316 and 317 ensuring continuous energization of the relay 314 with a resulting continuously closed state for the normally open contacts 316 and 317. The solenoid 140 is not energized due to the open circuit condition of the limit switch 318 and the open contacts 320 and 324.

When the limit switch 318 is sequentially closed by the triggering device 192 (FIG. 1) the solenoid 140 remains unenergized due to the open circuit condition of the contacts 320, held open by continuous energization of the counter 310 through the upper branch of the selector switch 308 and the open circuit condition of the normally open contact 324. The plunger 60 thus remains protracted during cyclic closings of the limit switches 306 and 318, the tire 20 being impacted one time for each revolution of the test wheel 12, and the counter 310 being pulsed each time the limit switch 306 closes. When the counter 310 has been pulsed ten times in accordance with the preselected counter setting, the counter contact 320, controlled by the counter 310 is permitted to assume its normally closed position. A subsequent closing of the limit switch 318 by the triggering device 192 (FIG. 1) permits the solenoid to be energized as current passes through the counter contact 320, the closed selector switch 322 to the solenoid 140 and the relay 326. Energization of the solenoid 140 enables air to flow to the side 188 of the cylinder 106 through the valve 136 to retract the plunger 60 in a manner previously described. Energization of the control relay 326 causes the normally closed contacts 312 to open and the normally open contacts 324 to close. The plunger 60 is thus held in a continuously retracted position as previously described.

While the counter 310 can be set to establish any number of impacts between the range of two and 100 a greater controlled number of impacts is obtainable by incorporating a counter with a greater count capacity.

If the tire 20 is to be cyclically impacted for an undetermined number of times the selector switch 304 is closed and the selector switches 308 and 322 are left in an open position. As previously described the solenoid 138 is energized when the limit switch 306 is closed causing protraction of the plunger 60. Since the selector switch 322 is in an open position the solenoid 140 cannot be energized despite cyclic closings of the limit switches 306 and 318. Thus the tire 20 will be impacted one time for each revolution of the test wheel 12 until the selector switch 322 is closed. A counting device of any suitable known construction arranged to count the number of revolutions of the test wheel 12 will provide a readout of the number of times the tire 20 is being impacted.

The circuit 300 thus functions as a device for preventing retraction of the plunger 60 from its protracted position for a predetermined number of revolutions of the test wheel 12 to effect a plurality of cyclic impacts to the tire 20 corresponding to the predetermined number of revolutions of the test wheel 12.

When the test wheel 12 is not being used for impact-testing the opening 62 in the wheel periphery 22 is sealed by unthreading and removing the plunger member 60 from the displacement member 72 and installing a plug member 200 (FIG. 6) which has a head portion 202 that threads directly into the opening 62. A pair of recesses 204, 204 in the plunger head portion 202 are engaged by any suitable spanner wrench (not shown) having prongs that fit into the recesses 204, 204 to facilitate threading or unthreading of the plug member 200 in the wheel periphery opening 62. The plug member 200 also includes a stem portion 206 that bottoms against the displacement member 72. A fastener 208 extends transversely through the annular collar 74 and the stem portion 206 to further maintain the plug in its sealed position in the opening 62. Access holes 210 and 212 (FIG. 2) in the spoke portions 36 and 52 permit access to the fastener 208.

As will be apparent to those skilled in the art the fixed structural components of the test wheel 12 can be welded together, cast or otherwise formed in any suitable known manner. The depth of penetration of the tire 20 during impact by the plunger 60 is dependent on the length of the plunger 60 and since the plunger 60 is threaded at 66 it can be interchanged with other plungers (not shown) of differing lengths or shapes to obtain different penetration depths of the tire during impact. The test wheel 12 and/or the tire 20 can be balanced in any suitable known manner.

Although the plunger 60 is pneumatically actuated into a protracted position the force of the tire 20 against the plunger 60 during impact is not transmitted back to the pneumatic cylinder 106. Due to the coplanar relationship between the longitudinal axis of the plunger 60, the central axis of the follower rod 76 and the central axis of the shaft 86 the plunger 60 does not shift or yield during any impact with the tire 20 and the impact forces of the tire 20 on the plunger 60 are transmitted directly to the shaft 86 which similarly does not shift or yield. Under this arrangement the plunger 60 is essentially locked into its protracted position despite any impact with the tire 20.

Some advantages of the present invention evident from the foregoing description include an apparatus for testing the dynamic impact resistance of a tire which apparatus can be set up in a laboratory for operation under predetermined conditions. The impact is delivered by a non-yielding plunger which can provide an accurate penetration at the tread center of the tire or at any other circumferential area of the tread or carcass. Further advantages include a test apparatus that warms up the tire, impacts it one or more times and continues to run the tire, if desired, without further impact. Still another advantage is an apparatus wherein a predetermined adjustable depth of impact penetration can be delivered to a moving tire. Another advantage is that the plunger can be removed and the peripheral opening in the test wheel plugged when no impact tests are desired.

In view of the above it will be seen that the several objects of the invention are achieved and other advantageous results attained.

As various changes could be made in the above constructions and methods without departing from the scope of the invention it is intended that all matter contained in the above description or shown in the accompanying drawings shall be interpreted as illustrative and not in a limiting sense.

What is claimed is:

1. An apparatus for testing the dynamic impact resistance of a tire comprising a frame, a wheel rotatably mounted on said frame and including a hub portion, said wheel having a generally circular peripheral surface with an opening, means for impacting a tire, said impact means being mounted on said wheel between said peripheral surface and said hub portion in alignment with the opening in said peripheral surface, means for protracting and retracting said impact means with respect to the opening in said peripheral surface, said protraction and retraction means comprising a reciprocable member and means for transmitting movement of said reciprocable member to said impact means to protract and retract said impact means, said movement transmission means comprising a cam member, and drive means for rotating said wheel on said frame during protraction and retraction of said impact means, and wherein said cam member is formed with a cam slot and is mounted on a shaft for rotation with said shaft, said impact means including a plunger member and a cam follower provided on said plunger member for engagement with said cam slot such that rotational movement of said cam member in one direction effects movement of said plunger member into a protracted position and rotational movement of said cam member in an opposite direction effects movement of said plunger member into a retracted position.

2. An apparatus for testing the dynamic impact resistance of a tire comprising a frame, a wheel rotatably mounted on said frame and including a hub portion, said wheel having a generally circular peripheral surface with an opening, means for impacting a tire, said impact means being mounted on said wheel between said peripheral surface and said hub portion in alignment with the opening in said peripheral surface, means for protracting and retracting said impact means with respect to the opening in said peripheral surface, said protraction and retraction means comprising a reciprocable member and means for transmitting movement of said reciprocable member to said impact means to protract and retract said impact means, said movement transmission means comprising a cam member, and drive means for rotating said wheel on said frame during protraction and retraction of said impact means, and wherein said movement transmission means comprise a rotatable shaft mounted on said wheel between said peripheral surface and said hub portion, said reciprocable member being eccentrically connected to a first portion of said shaft to rotate said shaft while reciprocating, said cam member being mounted on a second portion of said shaft for rotatable movement with said shaft during reciprocable movement of said reciprocable member.

3. An apparatus as claimed in claim 2 wherein said cam member is engageable with said impact means such that rotational movement of said cam member effects protractile movement of said impact means with respect to the opening in the peripheral surface of said wheel when said reciprocable member reciprocates in a first direction, rotational movement of said cam member effecting retractile movement of said impact means with respect to the opening in the peripheral surface of said wheels when said reciprocable member reciprocates in a direction opposite said first direction.

4. An apparatus for testing the dynamic impact resistance of a tire comprising a frame, a wheel rotatably mounted on said frame and including a hub portion, said wheel having a generally circular peripheral surface with an opening, means for impacting a tire, said impact means being mounted on said wheel between said peripheral surface and said hub portion in alignment with the opening in said peripheral surface, means for protracting and retracting said impact means with respect to the opening in said peripheral surface, and drive means for rotating said wheel on said frame during protraction and retraction of said impact means and wherein said protraction and retraction means include means for preventing retraction of said impact means from a protracted position for a predetermined number of revolutions of said wheel to effect a plurality of impacts to the tire corresponding to the predetermined number of wheel revolutions.

5. An apparatus for testing the dynamic impact resistance of a tire comprising a frame, a wheel rotatably mounted on said frame and including a hub portion, said wheel having a generally circular peripheral surface with an opening, means for impacting a tire, said impact means being mounted on said wheel between said peripheral surface and said hub portion in alignment with the opening in said peripheral surface, means for protracting and retracting said impact means with respect to the opening in said peripheral surface, and drive means for rotating said wheel on said frame during protraction and retraction of said impact means and wherein said protraction and retraction means comprise a double acting pneumatic air cylinder having a piston member connected to said impact means such that movement of said piston member in one direction protracts said impact means from the opening in said peripheral surface and movement of said piston member in the opposite direction retracts said impact means with respect to the opening in said peripheral surface.

6. An apparatus as claimed in claim 5 wherein said protraction and retraction means further include an electrically actuatable multi-position air control valve communicating with said pneumatic cylinder to govern the directional movement of said piston member and a control circuit means for actuating said air control valve into at least one of said multiple positions.

7. An apparatus as claimed in claim 6 wherein said control circuit means include means for preventing retraction of said impact means in said opening for a predetermined number of revolutions of said wheel to effect a plurality of impacts to the tire corresponding to the predetermined number of wheel revolutions.

8. An apparatus for testing the dynamic impact resistance of a tire comprising a frame, a wheel rotatably mounted on said frame and including a hub portion, said wheel having a generally circular peripheral surface with an opening, means for impacting a tire, said impact means being mounted on said wheel between said peripheral surface and said hub portion and including an impact member, means for protracting and retracting said impact member with respect to the opening in said peripheral surface such that said impact member moves back and forth along a common linear path with respect to said opening, and drive means for rotating said wheel on said frame during protraction and retraction of said impact member.

9. An apparatus as claimed in claim 8 wherein said protraction and retraction means comprise a cam.

10. An apparatus as claimed in claim 8 wherein said protraction and retraction means comprise a reciprocable member and means for transmitting reciprocable movement of said reciprocable member to said impact member to protract and retract said impact member.

11. An apparatus as claimed in claim 10 further including control circuit means for governing movement of said reciprocable member, said control circuit means including means for preventing retraction of said impact member in said opening for a predetermined number of revolutions of said wheel to effect a plurality of impacts to the tire corresponding to the predetermined number of wheel revolutions.

12. An apparatus as claimed in claim 10 wherein said means for transmitting reciprocable movement comprise a cam member.

13. An apparatus as claimed in claim 12 wherein said cam member is formed with a cam slot and is mounted on a shaft for rotation with said shaft, said impact means further including a cam follower provided on said impact member for engagement with said clam slot such that rotational movement of said cam member in one direction effects movement of said impact member into a protracted position and rotational movement of said cam member in an opposite direction effects movement of said impact member into a retracted position.

14. An apparatus as claimed in claim 12 wherein said means for transmitting reciprocable movement further comprise a rotatable shaft mounted on said wheel between said peripheral surface and said hub portion, said reciprocable member being eccentrically connected to a first portion of said shaft to rotate said shaft while reciprocating, said cam member being mounted on a second portion of said shaft for rotatable movement with said shaft during reciprocable movement of said reciprocable member.

15. An apparatus as claimed in claim 14 wherein said cam member is engageable with said impact member such that rotational movement of said cam member effects protractile movement of said impact member with respect to the opening in the peripheral surface of said wheel when said reciprocable member reciprocates in a first direction, rotational movement of said cam member effecting retractile movement of said impact member with respect to the opening in the peripheral surface of said wheel when said reciprocable member reciprocates in a direction opposite said first direction.

16. An apparatus as claimed in claim 8 wherein said impact member is removable and reengageable with said wheel, said apparatus further including a detachable plug member engageable with the opening in said wheel for sealing said opening when said impact member is removed.

17. An apparatus as claimed in claim 8 wherein said protraction and retraction means include means for preventing retraction of said impact member from a protracted position for a predetermined number of revolutions of said wheel to effect a plurality of impacts to the tire corresponding to the predetermined number of wheel revolutions.

18. An apparatus as claimed in claim 8 wherein said protraction and retraction means comprise a double acting pneumatic air cylinder having a piston member connected to said impact means such that movement of said piston member in one direction protracts said impact member from the opening in said peripheral surface and movement of said piston member in the opposite direction retracts said impact member with respect to the opening in said peripheral surface.

19. An apparatus as claimed in claim 18 wherein said protraction and retraction means further include an electrically actuatable multi-position air control valve communicating with said pneumatic cylinder to govern the directional movement of said piston member and a control circuit means for actuating said air control valve into at least one of said multiple positions.

20. An apparatus as claimed in claim 19 wherein said control means include means for preventing retraction of said impact member in said opening for a predetermined number of revolutions of said wheel to effect a plurality of impacts to the tire corresponding to the predetermined number of wheel revolutions.

21. An apparatus as claimed in claim 8 wherein said linear path is on a radius of said wheel.

22. A method for testing the dynamic impact resistance of a tire comprising rotating the tire about a first axis, rotating a wheel with a peripheral opening therein about a second axis and providing said wheel with an impact member, moving the impact member on a linear path with respect to the wheel opening in a first direction to protract the impact member through the opening to impact the tire while the tire and wheel are rotating, the respective axes of the tire and wheel being in a proximity with respect to each other to ensure impact of the tire when the impact member is protracted, and retracting the impact member in the wheel opening after impact with the tire by moving the impact member in a reverse direction on said linear path while the tire and wheel are rotating.

23. The method of claim 22 including programming automatic cyclic repetition of the impact step for a predetermined number of times.

* * * * *

UNITED STATES PATENT AND TRADEMARK OFFICE
CERTIFICATE OF CORRECTION

PATENT NO. : 3,986,392

DATED : October 19, 1976

INVENTOR(S) : HARALD L. STILLER, et al.

It is certified that error appears in the above-identified patent and that said Letters Patent are hereby corrected as shown below:

Claim 13, column 13, line 8, change "clam" to --cam--.

Claim 20, column 14, line 21, after "control" insert --circuit--.

Signed and Sealed this

Twenty-ninth Day of March 1977

[SEAL]

Attest:

RUTH C. MASON
Attesting Officer

C. MARSHALL DANN
Commissioner of Patents and Trademarks